United States Patent [19]

Denney

[11] Patent Number: 5,151,370
[45] Date of Patent: Sep. 29, 1992

[54] REAGENT AND METHOD FOR SERUM IRON ASSAY

[75] Inventor: Jerry W. Denney, Lachine, Canada

[73] Assignee: Synermed, Inc., Quebec, Canada

[21] Appl. No.: 596,942

[22] Filed: Oct. 11, 1990

[51] Int. Cl.$^5$ .............................................. G01N 33/52
[52] U.S. Cl. ........................................ 436/74; 436/84; 436/171; 422/61
[58] Field of Search .................. 436/74, 84, 171, 175, 436/910, 164; 422/61

[56] References Cited

U.S. PATENT DOCUMENTS

| | | | |
|---|---|---|---|
| 4,154,929 | 5/1979 | Outcalt et al. | 544/183 |
| 4,224,034 | 8/1980 | Denney | 23/230 |
| 4,308,027 | 12/1981 | Ceriotti | 23/230 B |
| 4,407,962 | 10/1983 | Tabacco | 436/74 |
| 4,703,015 | 10/1987 | Tabacco | 436/74 |
| 4,810,656 | 3/1989 | Torelli | 436/74 |

OTHER PUBLICATIONS

Garcia Clin. Chim. Acta, 94, 115-19 1979.
CA 103(7): 50885h "Determination of iron in blood serum by dual-wave length spectrophotometry", Jpn. Kokai Tokyo Koho, 4 pages 1985.

*Primary Examiner*—James C. Housel
*Assistant Examiner*—David Redding
*Attorney, Agent, or Firm*—Baker & Daniels

[57] ABSTRACT

A method utilizing a novel reagent for the assay (determination)of serum iron.

The serum iron assay reagent is a single, stable reagent, which includes the chromogen chromazurol B (CAB), chromazurol S (CAS), or an alkali metal, alkaline earth metal, rubidium or ammonium base addition salt of CAB or CAS, a surfactant that forms a ternary complex with iron and the chromogen, a buffer, and dimethylsulfoxide.

14 Claims, No Drawings

REAGENT AND METHOD FOR SERUM IRON ASSAY

FIELD OF INVENTION

This invention relates to the assay of serum iron in blood serum or heparinized plasma.

BACKGROUND OF THE INVENTION

In the blood, iron in its ferric oxidation state is bound to the protein transferrin. Normally, transferrin is only partially saturated with iron and serves to transport iron from the digestive tract to the blood forming organs, where iron is removed from transferrin and incorporated into hemoglobin. Unsaturated iron binding capacity (UIBC) is the measurement of the amount of transferrin that carries no iron, while serum iron is the measurement of the amount of iron that is bound to transferrin.

The assays of serum iron and UIBC are useful in diagnosing, differentiating and predicting various forms of anemia. The measurement of serum iron in combination with the measurement of UIBC allows the physician to determine which part of the body's pathway to hemoglobin synthesis is deficient, and with such knowledge the treatment of the anemia becomes apparent.

Abnormal serum iron and UIBC levels can be used to predict that anemia will occur in certain pregnancies due to poor absorption of folic acid from the digestive tract. The reason that these serum iron/UIBC changes occur before anemia has developed is due to the long half-life of erythrocytes in the blood. The hemoglobin level represents the adequacy of hemoglobin formation over several weeks prior to hemoglobin measurement, and serum iron/UIBC measurements indicate the current status of hemoglobin formation. Therefore, serum iron/UIBC measurements allow therapy to be implemented before anemia develops, thereby preventing injury to the mother or fetus.

Traditionally, serum iron has been assayed by adding a serum sample to a reagent buffered at an acid pH, which dissociated ferric ion from transferrin. The reagent included a reducing agent, which aided in the dissociation process and reduced ferric ion to ferrous ion. A chromogenic reagent was then added and the chromogen complexed with ferrous iron to form a colored complex, which was measured spectrophotometrically.

However, traditional serum iron assays have been problematic for several reasons. First, serum contains chromatic components, such as hemoglobin and bilirubin, which significantly absorb light at the measuring absorption wavelength of the iron-chromogen colored complex. Second, turbidity due to lipemia interferes with spectral measurements of serum iron. Third, reducing agents, such as thioglycollic acid and ascorbic acid, used in the assay are unstable. Fourth, cupric ion found in serum can compete with ferrous ion for complexing with the chromogen. Fifth, some serum components, such as bilirubin, citric acid, oxalic acid, phospholipids and proteins, can bind serum iron, thus preventing serum iron from complexing with the chromogen.

Certain improvements were made to the serum iron assay by Garcic, *Clin. Chim. Acta*, 94, 115–19 (1979) (hereinafter Garcic). Garcic discloses the use of the ammonium salt of the chromogen chromazurol B (also known as chrome azurol B; eriochrome azurol B; and mordant blue 1) (hereinafter CAB), and the surfactant cetyltrimethylammonium bromide (CTMA), which react with ferric ion to form a colored complex. The CAB-CTMA-iron ternary complex is spectrophotometrically measured at 630 nanometers (nm), a wavelength at which the chromatic components of serum either no longer interferingly absorb light or minimally absorb light (in the case of turbid samples). Further, Garcic claims cupric ion interference is negligible, which is disputed by Torelli (U.S. Pat. No. 4,810,656, col. 1, lines 11–26), and reducing agents are avoided. However, the serum iron assay requires a 20 minute reaction time, which is too long for automation. Although some automated analyzers can perform an assay that requires a reaction time longer than about 10 minutes, the overwhelming majority of commercially available automated analyzers (such as the Hitachi 704, 707, and 747 analyzers, and the Olympus AU 5000) cannot perform an assay that requires a reaction time longer than about 10 minutes, and a reaction time of less than 10 minutes is greatly preferred (see Takano et al., U.S. Pat. No. 4,588,695, col. 3, lines 29–31). Automation of the serum iron assay is highly desirable because it is one of the twenty most commonly performed medical diagnostic tests in clinical laboratories.

Another problem with the Garcic method is that protein interference is substantial. Protein interference must be subtracted from the measurement of a test sample by employing a serum blank comprised of serum, chromogenic reagent and a masking reagent that includes citric acid, which prevents formation of the CAB-CTMA-iron complex.

The Garcic method requires the preparation of the ammonium salt of CAB. Since the acid form of CAB is poorly soluble in water, the ammonium salt of CAB is prepared to impart sufficient solubility to CAB in aqueous solutions. To avoid the necessity of preparing the ammonium salt, Tabacco et al., U.S. Pat. No. 4,407,962 ('962), improved the Garcic method by adding ethanol to the chromogenic reagent to solubilize CAB in its acid form. Therefore, preparation of the ammonium salt of CAB is no longer necessary. However, a 20-minute reaction time is still required for the assay. Further, a serum blank with maskino reaoent is required to compensate for protein interference.

Tabacco et al., U.S. Pat. No. 4,703,015 ('015), discloses use of the chromogen chromazurol S (also known as chrome azurol S; mordant blue 29; and chromeazurol S) (hereinafter CAS) as a substitute for CAB in the chromogenic reagent for a serum iron assay. Although CAS has a slightly lower molar coefficient of extinction (molar absorptivity) than CAB, CAS is more soluble in aqueous medium and the addition of an organic solvent to the chromogenic reagent is not required. However, assay reaction time is 20 minutes; therefore, the assay is not automatable. Further, protein interference remains a problem, thus requiring a serum blank that includes a masking reagent, and interference from cupric ion may still be significant. Torelli. col. 1, lines 11–26.

Torelli disoloses a chromogenic reagent for serum iron assay that eliminates protein and cupric interferences. The reagent includes CAB, a surface active agent (such as CTMA) in a concentration of at least 500 milligrams (mg)/liter (l), a salt (preferably sodium chloride) in a concentration that imparts an ionic strength of at least 100 grams (g)/l (expressed in terms of sodium chloride concentration), and an amino acid, such as glycine, to eliminate cupric ion interference. However, the high salt concentration of this reagent is disadvantageous for automation because many automated analyzers wash and reuse reaction vessels. If sodium chloride is used, any salt residue remaining after washing of the reaction vessel will artificially elevate a subsequent serum analysis for sodium and chloride. Further, the high concentration of surface active agent lowers the molar absorptivity of the CAB-CTMA-iron ternary complex.

Denney et al., U.S. Pat. No. 4,224,034 ('034), and Outcalt et al., U.S. Pat. No. 4,154,929 ('929) disclose the use of dimethylsulfoxide (DMSO) in a serum iron assay to speed up the assay and to diminish turbidity due to lipemia and/or protein precipitation. '034 col. 4, lines 58–61 and col. 8, lines 33–42; '929 col. 4, lines 58–61 and col. 8, lines 38–47. The '034 and '929 patents do not teach the addition of DMSO to eliminate nonturbidity related protein interferences because a serum blank measurement is required by the assay methods. '034 col. 8, lines 43–61; '929 col. 8, lines 48–66. Further, the serum iron assay methods taught by the '034 and '929 patents employ the unstable reducing agent ascorbic acid. Also, the percentage of DMSO employed in the serum iron assay taught by '034 and '929 is 7% (vol.:vol.) in the final reaction mixture (10% vol.:vol. in the acetate buffer used in the assay). '034 col. 8, lines 45–50; '929 col. 8, lines 50–55.

OBJECTS OF THE INVENTION

One object of the invention is to provide a relatively quick serum iron assay that may be automated.

Another object of the invention is to provide a single, stable reagent for use in a serum iron assay.

Another object of the invention is to provide a serum iron assay that does not require a serum blank for the subtraction of protein interference.

Another object of the invention is to provide a serum iron assay that avoids interference from cupric iron.

Another object of the invention is to avoid incorporating unstable reducing agents into a reagent for serum iron assay.

Still other objects and advantages of the invention will become apparent to those of skill in the art after reading the following description of a preferred embodiment.

SUMMARY OF THE INVENTION

The invention provides an automatable method utilizing a novel reagent for the assay (determination) of serum iron.

The serum iron assay reagent is a single, stable reagent, which includes the chromogen chromazurol B (CAB), chromazurol S (CAS), or an alkali metal, alkaline earth metal, rubidium, or ammonium base addition salt of CAB or CAS, a surfactant that forms a ternary complex with iron and the chromogen, a buffer and dimethylsulfoxide. The inclusion of dimethylsulfoxide provides the multiple advantages of solubilizing the chromogen in its acid-form, eliminating interference from protein in serum, thereby eliminating the need for a serum blank with a masking reagent, and accelerating assay time, thereby making the serum iron assay automatable.

DESCRIPTION OF THE INVENTION

I. Serum Iron Reagent

The serum iron reagent is a single, stable reagent, meeting the following general requirements:

| General Requirements of Stock Serum Iron Reagent | |
|---|---|
| Ingredient | Amount of Ingredient per liter (l) of Aqueous Reagent |
| chromogen (CAB, CAS, or alkali metal, alkaline earth metal, rubidium, or ammonium salts thereof) | From about 0.01 to about 0.3 millimol (m mol) |
| a complexing surfactant (an alkylammonium halide or polyhydroxyalkylene ether) | about a 1:1 molar ratio of complexing surfactant to chromogen is preferred |
| a buffer that will not complex with iron | sufficient to maintain a pH of from about 4.5 to about 5.5 when the reagent is added to a serum sample |
| dimethylsulfoxide (DMSO) | from about 100 ml to about 300 ml |

The chromogen must be provided in sufficient concentration to react with all iron in a serum sample. CAB, CAS and their alkali metal, alkaline earth metal, rubidium and ammonium salts are highly sensitive chromogens (CAB and CAS have a high molar absorptivity.). However, CAB and its salts are preferred because of their slightly greater sensitivity (greater molar absorptivity).

A complexing surfactant, either an alkylammonium halide or a polyhydroxyalkylene ether, is added to the reagent to form the ternary complex, chromogen-complexing surfactant-iron, which is spectrophotometrically measured in the assay. The complexing surfactant must be provided in sufficient concentration so that it will react with all the binary complex, chromogen-iron, in the serum sample. Optimally, the molar ratio of complexing surfactant to chromogen is about 1:1. Increasing the amount of complexing surfactant above the 1:1 ratio only decreases the molar absorptivity of the ternary complex. Decreasing the amount of complexing surfactant below the 1:1 ratio runs the risk of having insufficient surfactant to form all of the ternary complex that can be formed, based upon the amount of iron available for complexation in a serum sample. The preferred complexing surfactant is cetyltrimethylammonium bromide (CTMA), also known as hexadecyltrimethylammonium bromide, which forms the ternary complex of CAB-CTMA-iron. The chromogen-complexing surfactant-iron complex is measured in the assay at a wavelength ($\lambda$) from about 630 nanometers (nm) to about 660 nm with a $\lambda$ of about 640 nm being preferred.

The inclusion of DMSO provides several advantages for the reagent and the assay of serum iron. DMSO shortens assay reaction time to a range of from about 3 minutes to about 10 minutes, thereby making the assay automatable on commercially available automated analyzers, which require assay reaction times of about 10 minutes or less.

DMSO solubilizes the acid-form of CAB. Therefore, preparation of an alkali metal, alkaline earth metal, or ammonium base addition salt of CAB is not required. However, if desired, a base addition salt of CAB may be used. Garcic (at page 116) discloses preparation of the ammonium salt of CAB. The preparation of other base addition salts of CAB is also contemplated by treatment of CAB with alkali metal and alkaline earth metal bases. For example, CAB may be treated with sodium hydroxide or potassium hydroxide to form a base addition salt.

Further, DMSO eliminates interference in the assay from serum protein. Therefore, a serum blank with or without a masking reagent is not required.

Although the amount of DMSO per liter of reagent may range from about 100 ml to about 300 ml, the preferred amount is about 200 ml. At about 200 ml per liter of reagent, the speed of the assay and protein interference are at a minimum. When the concentration of DMSO increases above about 300 ml/l reagent, the assay improves little, if any, and reagent cost increases due to the expense of DMSO.

Buffers, such as dicarboxylic acids, tricarboxylic acids (e.g. citric acid), ethylenediaminetetraacetic acid, and phosphates, that will complex with iron should be avoided. Any buffer that will provide a pH of from about 4.5 to about 5.5 and that will not complex with iron may be used. An acetic acid/sodium acetate buffer will achieve this pH range, will not complex with iron, and is preferred because it is inexpensive.

Although interference from cupric ion has not been observed in the assay of serum iron based upon the above reagent, thiourea, which prevents interference from cupric ion, may be optionally included in the serum iron reagent in at least about 0.1 g thiourea/1 of serum iron reagent to safeguard against cupric ion interference in the serum sample.

Because serum components, such as bilirubin, citric acid, oxalic acid, phospholipids, and proteins have the potential for binding serum iron, an inorganic alkali metal salt or an alkaline earth metal salt, preferably a magnesium halide and most preferably magnesium chloride, is added to the serum iron reagent to provide these serum components with a cationic complexing agent other than iron. The addition of such a salt to the reagent is preferred but not required.

A preferred serum iron reagent is prepared by the following steps:
1) add about 765 mg of CAS (available from Chemical Dynamics and from Fluka Chemika-BioChemika; molecular weight=605.29) to about 200 ml of DMSO and mix to form a first solution;
2) add iron-free water to the first solution to bring the total volume to about 800 ml, thereby forming a second solution;
3) add from about 0.33 mol to about 0.39 mol potassium hydroxide or sodium hydroxide and about 37 g of glacial acetic acid to the second solution and mix until dissolved, thereby forming a third solution;
4) add about 270 mg of CTMA to the third solution and stir until dissolved, thereby forming a fourth solution;
5) add about 20 g of magnesium chloride hexahydrate (about 98 m mol magnesium chloride) to the fourth solution and stir until dissolved, thereby forming a fifth solution;
6) add iron-free water to the fifth solution until a volume of 1 liter is achieved, thereby forming the serum iron reagent.

The inventive reagent may also be supplied as a diagnostic kit for use in automated chemical analyzers, particularly the Hitachi 705 automated biochemistry analyzer.

Generally, the diagnostic kit is comprised of first and second compositions. At a minimum, the first composition includes a first portion of DMSO and iron-free water. The second composition includes a second portion of DMSO, chromogen, buffer, complexing surfactant, and iron-free water. When the first and second compositions are combined, as described in Serum Iron Assay Method below, the concentration of DMSO is within the above-stated concentration range for the inventive reagent (from about 100 ml DMSO to about 300 ml DMSO per liter of reagent).

More preferably, the first composition will include thiourea to safeguard against cupric ion interference, and a polyoxyethylenesorbitan surfactant. The second composition will more preferably include thiourea and an inorganic salt selected from the group described above. Most preferably, the polyoxyethylenesorbitan surfactant will be polyoxyethylenesorbitan monooleate (TWEEN 80 available from Sigma Chemical Company).

A particularly preferred diagnostic kit for the Hitachi 705 analyzer may be made as follows:

First Composition (R1)

Step 1—Add iron-free water to about 192 g DMSO until a volume of about 500 ml is achieved.
Step 2—Add about 0.1 g thiourea and about 0.5 ml polyoxyethylenesorbitan monooleate and mix until a solution is formed.
Step 3—Add iron-free water until a volume of about one liter is achieved.

Second Composition (R2)

Step 1—Mix about 436 g DMSO with about 1 m mol CAB (about 635 mg of approximately 80% CAB available from Sigma Chemical Company) until a solution is formed.
Step 2—Add iron-free water until a total volume of about 750 ml is achieved.
Step 3—Add from about 1.3 mol to about 1.6 mol of potassium hydroxide or sodium hydroxide, about 147 g glacial acetic acid, about 0.1 g thiourea, about 2 g hexadecyltrimethylammonium bromide, about 2 g magnesium chloride and mix until a solution is formed.
Step 4—Add iron-free water until total volume is about one liter.

Substituting an equivalent molar amount of any ingredient above with another ingredient within the same category given under General Requirements of Stock Serum Iron Reagent (i.e., any of the chromagens, complexing surfactants, and buffers listed under General Requirements of Stock Serum Iron Reagent) will yield an acceptable diagnostic kit that may be used in an automatable assay.

II. Serum Iron Assay Method

An assay for serum iron requires the serum iron reagent (disclosed above) and an iron standard containing a known amount of iron. At a minimum, the iron standard for an iron assay that utilizes the chromogens CAS and CAB (and their salts as described above) should contain transferrin, ferric ion from a ferric salt, such as ferric chloride, and iron-free water.

A preferred iron standard may be prepared by adding iron-free water to a known amount of ferric ions (for example, from ferric chloride) and an additive, such as hydrochloric acid, that helps prevent reduction of ferric ion to ferrous ion, to form an iron-containing solution of known volume. The ferric ions must be in sufficient amount to achieve a concentration of ferric ions within the dynamic concentration range for iron in serum (the concentration range of iron that will be found in serum). A satisfactory iron-containing solution contains 400 micrograms (μg) of iron per deciliter (dl) of solution. Such a solution may be prepared by adding 116.2 mg ferric chloride (anhydrous) to a 10 l volumetric flask. Ten (10) ml of concentrated hydrochloric acid is then added to the flask followed by the addition of deionized water until a volume of 10 l is obtained.

Generally, the assay method is comprised of the following steps:

a. adding a serum sample to the serum iron reagent followed by mixing to form a test sample;

b. adding iron-free water to the serum iron reagent followed by mixing to form a test blank;

c. adding iron standard to the serum iron reagent to form a test standard;

d. incubating the test sample, the test blank, and the test standard at about 37° C. from about 3 minutes to about 10 minutes;

e. spectrophotometrically determining absorbances (A) of the test sample, the test blank, and the test standard; and f. calculating the concentration of iron in the test sample by the following equation:

$$\frac{A_{test\ sample} - A_{test\ blank}}{A_{test\ standard} - A_{test\ blank}} \times$$

known concentration of iron in the test standard = concentration of iron in the test sample.

Absorbances are preferably measured at 640 nanometers (nm), and may be measured on automated chemistry analyzers using filters having mean wavelength band passes from about 630 nm to about 660 nm.

Importantly, the assay requires only about a three minute incubation period (reaction time), thereby easily making the method automatable. Further, the assay does not require the use of a serum blank with or without a masking reagent for the subtraction of protein interference. The serum iron reagent employed in the assay eliminates such protein interference, thereby making the assay method simpler and more accurate than other serum iron assay methods.

Lipemia in serum can still cause error in the assay due to turbidity. Such error can be corrected by automated bichromatic correction means involving spectrophotometrically determining absorbances of the test sample and test blank at a primary wavelength (1°λ) from about 630 nm to about 660 nm (preferably at about 640 nm), followed by spectrophotometric measurement of those samples at a secondary wavelength (2°λ) from about 680 nm to about 850 nm (preferably at about 700 nm). Correction for turbidity in lipemic serum is then made by the following calculation which is substituted for the absorbance measurements in the numerator of the above equation for determining concentration of the test sample:

($A$ test sample 1°λ − $A$ test blank 1°λ) −
                 ($A$ test sample 2°λ − $A$ test blank 2°λ).

This bichromatic measurement corrects for error due to turbidity because absorbance due to turbidity remains relatively constant from the 1°λ to the 2°λ, while absorbance of the chromogen-complexing surfactant-iron complex decreases dramatically from the 1°λ to the 2°λ.

Therefore, subtraction of absorbances at 2°λ from absorbances at 1°λ yields absorbance due to the chromogen-iron-surfactant complex.

Another means of correcting lipemic serum samples is to analyze a separate serum blank without a masking reagent. The serum blank without masking reagent would include a second serum sample (same volume and serum pool as serum sample in the test sample) and iron-free water (same volume as serum iron reagent) and would be incubated and spectrophotometrically measured analogously to the test sample, test blank and test standard. The concentration of iron in the test sample would then be calculated by the following equation:

$$\frac{A_{test\ sample} - (A_{test\ blank} + A_{serum\ blank\ without\ masking\ reagent})}{A_{test\ standard} - A_{test\ blank}} \times$$

known concentration of iron in the test standard = concentration of iron in the test sample Alternatively, incubation may be conducted at ambient temperature. However, the assay is faster and more accurate at 37° C. (see Tabacco et al., *Clin. Chim. Acta,* 114, 287, 289 (Table II) (1981)). Heparinized plasma may also be used instead of serum for the test sample and the serum blank without masking reagent.

Specifically, an assay may be performed with the preferred serum iron reagent by employing the following amounts of ingredients in the method stated above: 2 ml serum iron reagent, 0.1 ml iron-free water, 0.1 ml iron standard, 0.1 ml serum sample.

A widely used clinical analyzer is the Hitachi 705 automated biochemistry analyzer. A serum iron assay method, which utilizes the present inventive reagent, may be performed using the Hitachi 705 analyzer. Use of the Hitachi 705 to perform an assay illustrates the use of both bichromatic correction means and dynamic serum blank means for correcting error due to lipemia. (In a dynamic serum blank, the same serum sample is sequentially used for both the spectrophotometric blank measurement and color measurement. In a true serum blank, as described above, the serum sample is divided into two portions, one portion is used for spectrophotometric blank measurement and the other portion is used for color measurement.)

To perform an assay on the Hitachi 705 analyzer, a serum sample is diluted with reagent R1 (see Serum Iron Reagent section) to form a test blank. Spectrophotometric readings are then performed on the blank at 660 nm (1°λ) and 700 nm (2°λ). Following these spectrophotometric measurements, reagent R2 is added to form a test sample. The test sample includes the inventive reagent and is incubated for about 5 minutes. Following incubation, spectrophotometric measurements are performed on the test sample at 660 nm (1°λ) and 700 nm (2°λ). The specific instrument settings for the Hitachi 705 analyzer are as follows:

| Chemistry Parameters for the Hitachi 705 | |
|---|---|
| Test: | Iron |
| Assay Code: | Endpoint |
| Sample Volume (μl): | 20 |
| R1 Volume (μl): | 350 |
| R2 Volume (μl): | 100 |
| R3 Volume: | |
| Wavelength 1: | 700 nm |
| Wavelength 2: | 660 nm |

-continued

| Chemistry Parameters for the Hitachi 705 | |
| --- | --- |
| Rgt. Blk. Abs.: | — |
| Rgt. Blk. Conc.: | 0 |
| Std. Conc.: | *** |
| Factor: | — |
| Std. Abs. Allowance: | 10% |
| Normal Range L: | |
| Normal Range H: | |
| Abs. Limit (Rate): | |
| Control I.D. No. | *** |

***Denotes user specifier settings
—Determined by instrument

Under the parameter settings given above, the analyzer performs bichromatic spectrophotometric measurements on the test blank, test sample, and a test standard of known iron concentration. The concentration of iron in the test sample is calculated by the equation $$\frac{(A_{test\ sample\ 1^*\lambda} - A_{test\ blank\ 1^*\lambda}) - (A_{test\ sample\ 2^*\lambda} - A_{test\ blank\ 2^*\lambda})}{A_{test\ standard\ 1^*\lambda} - A_{test\ standard\ 2^*\lambda}} \times$$

known concentration of iron in the test standard = concentration of iron in the test sample.

I claim:

1. A method for the assay of iron in lipemic serum or heparinized plasma, comprising the steps of:
   a. preparing a test sample by adding a first serum sample or heparinized plasma sample to the reagent comprising:
      (1) a chromogen selected from the group consisting of chromazurol B, chromazurol S, and alkali metal, alkaline earth metal, rubidium, or ammonium salts thereof;
      (2) a complexing surfactant selected from the group consisting of alkylammonium halides and polyhydroxyalkylene ethers;
      (3) a buffer that will not complex iron and will provide a pH of from about 4.5 to about 5.5; and
      (4) dimethylsulfoxide in an amount sufficient to solubilize the chromogen, eliminate protein interference in serum or heparinized plasma, and achieve an incubation time in the assay of from about 3 minutes to about 10 minutes;
   b. preparing a test blank by ading iron-free water to said reagent;
   c. preparing a test standard by adding an iron standard of known iron concentration to said reagent;
   d. preparing a serum blank or heparinized plasma blank without masking reagent by adding a second serum sample or heparinized plasma sample to iron-free water;
   e. incubating the test sample, the test blank, the test standard, and the serum blank or heparinized plasma blank without masking reagent at about 37° C. for at least about three minutes;
   f. spectrophotometrically measuring absorbances (A) of the test sample, the rest blank, the test standard, and the serum blank or heparinized plasma blank without masking reagent; and
   g. calculating the concentration of iron in the test sample by the equation $$\frac{A_{test\ sample} - (A_{test\ blank} + A_{serum\ blank\ or\ plasma\ blank})}{A_{test\ standard} - A_{test\ blank}} \times$$

known concentration of iron in the test standard = concentration of iron in the test sample.

2. A method for the assay of iron in lipemic serum or heparinized plasma, comprising the steps of:
   a. preparing a test sample by adding a first serum sample or heparinized plasma sample to a reagent comprising:
      (1) a chromogen selected from the group consisting of chromazurol B, chromazurol S, and alkali metal, alkaline earth metal, rubidium, or ammonium salts thereof;
      (2) a complexing surfactant selected from the group consisting of alkylammonium halides and polyhydroxyalkylene ethers;
      (3) a buffer that will not complex iron and will provide a pH of from about 4.5 to about 5.5; and
      (4) 100 ml/l reagent to about 300 ml/l reagent of dimethylsulfoxide to solubilize the chromogen, eliminate protein interference in serum or heparinized plasma, and achieve an incubation time in the assay of from about 3 minutes to about 10 minutes;
   b. preparing a test blank by adding iron-free water to said reagent;
   c. preparing a test standard by adding an iron standard of known iron concentration to said reagent;
   d. preparing a serum blank or heparinized plasma blank without masking reagent by adding a second serum sample or heparinized plasma sample to iron-free water;
   e. incubating the test sample, the test blank, the test standard, and the serum blank or heparinized plasma blank without masking reagent at about 37° C. for at least about three minutes;
   f. spectrophotometrically measuring absorbances (A) of the test sample, the test blank, the test standard, and the serum blank or heparinized plasma blank without masking reagent; and
   g. calculating the concentration of iron in the test sample by the equation $$\frac{A_{test\ sample} - (A_{test\ blank} + A_{serum\ blank\ or\ plasma\ blank})}{A_{test\ standard} - A_{test\ blank}} \times$$

known concentration of iron in the test standard = concentration of iron in the test sample.

3. A method for the assay of iron in lipemic serum or heparinized plasma, comprising the steps of:
   a. spectrophotometrically measuring the absorbance (A) of a dynamic blank of serum or heparinized plasma without masking reagent;
   b. preparing a test blank by adding iron-free water to a reagent comprising:
      (1) a chromogen selected from the group consisting of chromazurol B, chromazurol S, and alkali metal, alkaline earth metal, rubidium, or ammonium salts thereof;
      (2) a complexing surfactant selected from the group consisting of alkylammonium halides and polyhydroxyalkylene ethers;
      (3) a buffer that will not complex iron and will provide a pH of from about 4.5 to about 5.5; and
      (4) dimethylsulfoxide in an amount sufficient to solubilize the chromogen, eliminate protein interference in serum or heparinized plasma, and achieve an incubation time in the assay of from about 3 minutes to about 10 minutes;
c. preparing a test sample by adding the dynamic blank to said reagent;
d. preparing a test standard by adding an iron standard of known iron concentration to said reagent;
e. incubating the test sample, test blank and test standard at about 37° C. for at least about three minutes;
f. spectrophotometrically measuring absorbances (A) of the test sample, test blank and test standard; and
g. calculating the concentration of iron in the test sample by the equation $$\frac{A_{test\ sample} - (A_{test\ blank} + A_{dynamic\ blank})}{A_{test\ standard} - A_{test\ blank}} \times$$

known concentration of iron in test standard = concentration of iron in the test sample.

4. A method for the assay of iron in lipemic serum or heparinized plasma, comprising the steps of:
a. spectrophotometrically measuring the absorbance (A) of a dynamic blank of serum or heparinized plasma without masking reagent;
b. preparing a test blank by adding iron-free water to a reagent comprising:
   (1) a chromogen selected from the group consisting of chromazurol B, chromazurol S, and alkali metal, alkaline earth metal, rubidium, or ammonium salts thereof;
   (2) a complexing surfactant selected from the group consisting of alkylammonium halides and polyhydroxyalkylene ethers;
   (3) a buffer that will not complex iron and will provide a pH of from about 4.5 to about 5.5; and
   (4) 100 ml/l reagent to about 300 ml/l reagent of dimethylsulfoxide to solubilize the chromogen, eliminate protein interference in serum or heparinized plasma, and achieve an incubation time in the assay of from about 3 minutes to about 10 minutes;
c. preparing a test sample by adding the dynamic blank to said reagent;
d. preparing a test standard by adding an iron standard of known iron concentration to said reagent;
e. incubating the test sample, test blank and test standard at about 37° C. for at least about three minutes;
f. spectrophotometrically measuring absorbances (A) of the test sample, test blank and test standard; and
g. calculating the concentration of iron in the test sample by the equation $$\frac{A_{test\ sample} - (A_{test\ blank} + A_{dynamic\ blank})}{A_{test\ standard} - A_{test\ blank}} \times$$

known concentration of iron in test standard = concentration of iron in the test sample.

5. The method of claims 2 or 4 in which the alkali earth metal of the reagent is magnesium chloride.

6. The method of claim 4 in which the reagent further comprises at least about 0.1 g thiourea/l reagent.

7. A method for the assay of iron in lipemic serum or heparinized plasma, comprising the steps of:
a. preparing a test sample by adding a first serum sample to the reagent comprising:
   a. about 765 mg chromazurol S/l reagent;
   b. about 200 ml dimethylsulfoxide/l reagent;
   c. from about 0.33 mol to about 0.39 mole potassium hydroxide or sodium hydroxide/l reagent;
   d. about 37 g glacial acetic acid/l reagent;
   e. about 270 mg cetyltrimethylammonium bromide/l reagent;
   f. about 98 millimole magnesium chloride/l reagent; and
   g. iron-free water in an amount sufficient to bring reagent volume to about 1 liter
b. preparing a test blank by adding iron-free water to said reagent;
c. preparing a test standard by adding an iron standard of known iron concentration to said reagent;
d. preparing a serum blank or heparinized plasma blank without masking reagent by adding a second serum standard or heparinized plasma sample to iron-free water;
e. incubating the test sample, the test blank, the test standard, and the serum blank or heparinized plasma blank without masking reagent at about 37° C. for at least about three minutes;
f. spectrophotometrically measuring absorbances (A) of the test sample, the test blank, the test standard, and the serum blank or heparinized plasma blank without masking reagent; and
g. calculating the concentration of iron in the test sample by the equation $$\frac{A_{test\ sample} - (A_{test\ blank} + A_{serum\ blank\ or\ plasma\ blank})}{A_{test\ standard} - A_{test\ blank}} \times$$

known concentration of iron in the test standard = concentration of iron in the test sample.

8. A method or the assay of iron in lipemic serum or heparinized plasma, comprising the steps of:
a. spectrophotometrically measuring the absorbance (A) of a dynamic blank of serum or heparinized plasma without masking reagent;
b. preparing a test blank by adding iron-free water to a reagent comprising:
   a. about 765 mg chromazurol s/l reagent;
   b. about 200 ml dimethylsulfoxide/l reagent;
   c. from about 0.33 mole to about 0.39 mole potassium hydroxide or sodium hydroxide/l reagent;
   d. about 37 g glacial acetic acid/l reagent;
   e. about 270 mg cetyltrimethylammoniumbromide/l reagent;
   f. about 98 millimole magnesium chlloride/l reagent; and
   g. iron-free water in an amount sufficient to bring reagent volume to about 1 liter;
c. preparing a test sample by adding the dynamic blank to said reagent;
d. preparing a test standard by adding an iron standard of known iron concentration to said reagent;
e. incubating the test sample, test blank and test standard at about 37° C. for at least about three minutes;
f. spectrophotometrically measuring absorbances (A) of the test sample, test blank and test standard; and
g. calculating the concentration of iron in the test sample by the equation $$\frac{A_{test\ sample} - (A_{test\ blank} + A_{dynamic\ blank})}{A_{test\ standard} - A_{test\ blank}} \times$$

known concentration of iron in test standard = concentration of iron in the test sample.

9. A diagnostic kit for the assay of iron in serum or heparinized plasma, comprising:
   a. a first composition comprised of a first portion of dimethylsulfoxide and iron-free water; and
   b. a second composition comprised of
      (1) a chromogen selected from the group consisting of chromazurol B, chromazurol S, and alkali metal, alkaline earth metal, rubidium, or ammonium salts thereof;
      (2) a second portion of dimethylsulfoxide, the first and second portions of dimethylsulfoxide being in a sufficient amount, when added together, to solubilize the chromogen, eliminate protein interference in serum or heparinized plasma, and achieve an incubation time in the assay of about 5 minutes or less;
      (3) a buffer that will not complex with iron and will provide a pH of from about 4.5 to about 5.5;
      (4) a complexing surfactant selected from the group consisting of alkylammonium halides and polyhydroxyalkylene ethers; and
      (5) iron-free water.

10. The diagnostic kit of claim 9, wherein the first composition further comprises at least about 0.1 g thiourea/l and about 0.5 ml of a polyoxyethylenesorbitan surfactant/l, and the second composition further comprises at least about 0.1 g thiourea/l and an inorganic salt selected from the group consisting of alkali metal and alkaline earth metal salts.

11. A method for the assay of iron in serum or heparinized plasma, comprising the steps of:
   a. preparing a test blank by adding a serum sample or heparinized plasma sample to a first composition comprised of a first portion of dimethylsulfoxide and iron-free water;
   b. spectrophotometrically measuring absorbance of the test blank at a primary wavelength $(1°\lambda)$ and a secondary wavelength $(2°\lambda)$;
   c. preparing a test sample by adding the test blank to second composition comprised of:
      (1) a chromogen selected from the group consisting of chromazurol B, chromazurol S, and alkali metal, alkaline earth metal, rubidium, or ammonium salts thereof;
      (2) a second portion of dimethylsulfoxide, the first and second portions of dimethylsulfoxide being in a sufficient amount, when added together, to solubilize the chromogen, eliminate protein interference in serum or heparinized plasma, and achieved an incubation time in the assay of about 5 minutes or less;
      (3) a buffer that will not complex with iron and will provide a pH of from about 4.5 to about 5.5;
      (4) a complexing surfactant selected from the group consisting of alkylammonium halides and polyhydroxyalkylene ethers; and
      (5) iron-free water
   d. spectrophotometrically measuring absorbance of the test sample at the primary wavelength $(1°\lambda)$ and the secondary wavelength $(2°\lambda)$;
   e. spectrophotometrically measuring absorbance of a test standard of known iron concentration at the primary wavelength $(1°\lambda)$ and the secondary wavelength $(2°\lambda)$;
   f. calculating the concentration of iron in the test sample by the equation $$\frac{(A_{test\ sample}\ 1°\lambda - A_{test\ blank}\ 1°\lambda) - (A_{test\ sample}\ 2°\lambda - A_{test\ blank}\ 2°\lambda)}{A_{test\ standard}\ 1°\lambda - A_{test\ standard}\ 2°\lambda} \times$$

known concentration of iron in the test standard = concentration of iron in the test sample.

12. A diagnostic kit for the assay of iron in serum or heparinized plasma, comprising:
   a. a first composition, which per liter comprises about 192 g dimethylsulfoxide, about 0.1 g thiourea, about 0.5 ml polyoxyethylenesorbitan monooleate, and iron-free water; and
   b. a second composition, which per liter comprises about 436 g dimethylsulfoxide, about 1 millimole of a chromogen selected from the group consisting of chromazurol B, chromazurol S, and alkali metal, alkaline earth metal, rubidium, or ammonium salts thereof, from about 1.3 mole to about 1.6 mole potassium hydroxide or sodium hydroxide, about 147 g glacial acetic acid, about 0.1 g thiourea, about 2 g hexadecyltrimethylammonium bromide, and about 2 g magnesium chloride.

13. The diagnostic kit of claim 12, wherein the chromogen is chromazurol B.

14. A method for the assay of iron in serum or heparinized plasma, comprising the steps of:
   a. preparing a test blank by adding a serum sample or heparinized plasma sample to a first composition, which per liter comprises about 192 g dimethylsulfoxide, about 0.1 g thiourea, about 0.5 ml polyoxyethylenesorbitan monooleate, and iron-free water;
   b. spectrophotometrically measuring absorbance of the test blank at a primary wavelength $(1°\lambda)$ and a secondary wavelength $(2°\lambda)$;
   c. preparing a test sample by adding the test blank to a second composition, which per liter comprises about 436 g dimethylsulfoxide, about 1 millimole of a chromogen selected from the group consisting of chromazurol B, chromazurol S, and alkali metal, alkaline earth metal, rubidium, or ammonium salts thereof; from about 1.3 mole to about 1.6 mole potassium hydroxide or sodium hydroxide, about 147 g glacial acetic acid, about 0.1 g thiourea, about 2 g hexadecyltrimethylammoniumbromide, and about 2 g magnesium chloride;
   d. spectrophotometrically measuring absorbance of the test sample at the primary wavelength $(1°\lambda)$ and the secondary wavelength $(2°\lambda)$;
   e. spectrophotometrically measuring absorbance of a test standard of known iron concentration at the primary wavelength $(1°\lambda)$ and the secondary wavelength $(2°\lambda)$;
   f. calculating the concentration of iron in the test sample by the equation $$\frac{(A_{test\ sample}\ 1°\lambda - A_{test\ blank}\ 1°\lambda) - (A_{test\ sample}\ 2°\lambda - A_{test\ blank}\ 2°\lambda)}{A_{test\ standard}\ 1°\lambda - A_{test\ standard}\ 2°\lambda} \times$$

known concentration of iron in the test standard = concentration of iron in the test sample.

* * * * *